United States Patent
Tsai et al.

(10) Patent No.: US 11,062,451 B2
(45) Date of Patent: Jul. 13, 2021

(54) SYSTEM AND METHOD FOR REAL-TIME DETERMINATION OF HAND BONE AGE USING PERSONAL DEVICE

(71) Applicant: Ever Fortune.AI CO., Ltd., Taichung (TW)

(72) Inventors: Fuu-Jen Tsai, Taichung (TW);
Tzung-Chi Huang, Taichung (TW);
Ken Ying-Kai Liao, Taichung (TW);
Chi-Kun Wang, Taichung (TW)

(73) Assignee: EVER FORTUNE.AI CO., LTD., Taichung (TW)

( * ) Notice: Subject to any disclaimer, the term of this patent is extended or adjusted under 35 U.S.C. 154(b) by 146 days.

(21) Appl. No.: 16/664,022

(22) Filed: Oct. 25, 2019

(65) Prior Publication Data

US 2021/0042921 A1 Feb. 11, 2021

(30) Foreign Application Priority Data

Aug. 5, 2019 (TW) .................................. 108127752

(51) Int. Cl.
| | |
|---|---|
| *G06K 9/00* | (2006.01) |
| *G06T 7/00* | (2017.01) |
| *G16H 30/20* | (2018.01) |
| *G06N 3/08* | (2006.01) |
| *G06N 20/00* | (2019.01) |

(52) U.S. Cl.
CPC .............. *G06T 7/0014* (2013.01); *G06N 3/08* (2013.01); *G06N 20/00* (2019.01); *G16H 30/20* (2018.01); *G06T 2207/10116* (2013.01); *G06T 2207/20081* (2013.01); *G06T 2207/20084* (2013.01); *G06T 2207/30008* (2013.01)

(58) Field of Classification Search
CPC ................................ G06N 20/00; G06N 3/08; G06T 2207/10116; G06T 2207/20081; G06T 2207/20084; G06T 2207/30008; G06T 7/0014; G16H 30/20; G16H 30/40; G16H 50/20; G16H 50/50
See application file for complete search history.

(56) References Cited

U.S. PATENT DOCUMENTS

| | | | |
|---|---|---|---|
| 2018/0232603 A1* | 8/2018 | Shim | ..................... A61B 6/00 |
| 2020/0020097 A1* | 1/2020 | Do | ..................... G06N 3/0454 |
| 2021/0034905 A1* | 2/2021 | Lee | ..................... G06K 9/6274 |
| 2021/0142477 A1* | 5/2021 | Tsai | ..................... G16H 30/40 |

* cited by examiner

*Primary Examiner* — Xin Jia
(74) *Attorney, Agent, or Firm* — Birch, Stewart, Kolasch & Birch LLP

(57) ABSTRACT

A system for real-time determination of the hand bone age using a personal device essentially include: a cloud computing platform storing a first marked database, an artificial neural network-based bone age model, and a comparison logic, wherein the first marked database at least has a hand bone image and the corresponding feature marking data; and a to-be-compared image providing device for downloading a to-be-compared hand bone image from a cloud-based to-be-compared image database. A personal device can be used to obtain a to-be-compared hand bone image from the to-be-compared image providing device and upload this image to the cloud computing platform in order for the cloud computing platform to find, through comparison, the hand bone image in the bone age model that is the most similar to the uploaded image and then transmit to the personal device the interpretation data corresponding to the hand bone image found.

10 Claims, 8 Drawing Sheets

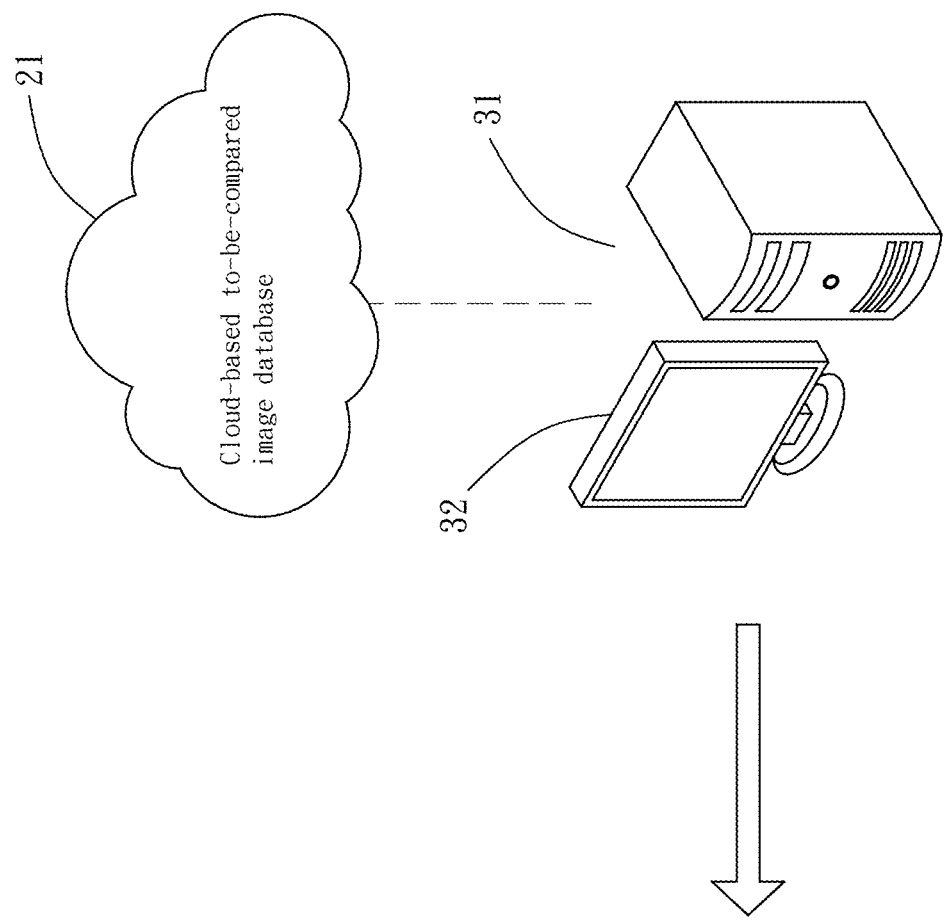
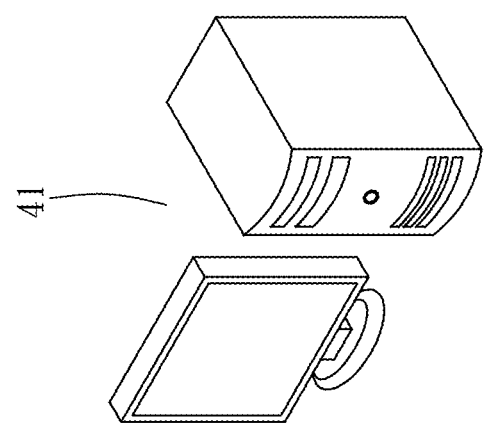
FIG. 3

SYSTEM AND METHOD FOR REAL-TIME DETERMINATION OF HAND BONE AGE USING PERSONAL DEVICE

BACKGROUND OF THE INVENTION

1. Technical Field

The present invention relates to online real-time interpretation of medical images by cloud computing. More particularly, the invention relates to a system and method for determining the hand bone age in real time using a personal device.

2. Description of Related Art

According to the prior art, a physician's expertise is called for to determine a person's bone age from an X-ray image of the person's hand bones; however, even an experienced physician would need to spend a lot of time flipping through a standard atlas in order to determine the bone age of a hand bone image. Clinically, a physician may have to explain to a large number of consulters or patients the interpretation results of their hand bone radiograms (wherein the results may be normal or otherwise), and the time required to explain to one whose bone age is determined to be normal may be as long as that required for one whose bone age is determined to be abnormal. If the physician has not a few appointments, his or her consulters or patients are bound to wait for a long time, and the physician may end up worn out, both physically and mentally. If, therefore, artificial intelligence (AI) in medicine can help shorten the time needed for image interpretation, the same physician will have more time to not only make accurate interpretations, but also address each consulter's or patient's concerns in depth.

Currently, an AI-based image interpretation system for medical use typically requires a supercomputer (as the main computing center) and a dedicated digital database of accurately marked medical images (as the source of reference information). In terms of application, it is common practice to connect such a system to the computers in multiple examination rooms in a hospital through the intranet of the hospital, and only a physician or medical practitioner is allowed to use the equipment and make AI-based interpretations. As the system is a closed system and affordable only to a large hospital, physicians working in a hospital without a supercomputer and a dedicated database of accurately marked medical images cannot but use the conventional human interpretation method, which is nevertheless time-consuming and labor-intensive as stated above.

BRIEF SUMMARY OF THE INVENTION

In view of the fact that the prior art is applicable only to a closed system with a supercomputer and is not open for use by physicians and hospitals outside the system, the inventor of the present invention proposes a system and method for determining the hand bone age in real time using a personal device and thereby solving the aforesaid problems of the prior art. The invention allows a physician's personal device to be the means by which to obtain the reference information required for real-time determination of the hand bone age and to further determine the hand bone age according to the reference information obtained.

To solve the foregoing problems, the present invention provides a system for determining the hand bone age in real time using a personal device. The system includes a cloud computing platform, a cloud-based to-be-compared image database, a to-be-compared image providing device, and a personal device. The cloud computing platform has a storage unit. The storage unit stores a first marked database, a bone age model, and a comparison logic. The cloud computing platform is configured to execute the comparison logic. The first marked database has plural entries of marked hand-bone image data. Each entry of marked hand-bone image data at least has a hand bone image and plural entries of feature marking data corresponding to the hand bone image. The bone age model is established by training an artificial neural network with the plural entries of marked hand-bone image data and has not only a plurality of hand bone images corresponding respectively to the plural entries of marked hand-bone image data, but also the interpretation data corresponding to each hand bone image in the bone age model. The cloud-based to-be-compared image database stores a plurality of to-be-compared hand bone images. The to-be-compared image providing device is coupled to the cloud-based to-be-compared image database and is configured to download one of the to-be-compared hand bone images in the cloud-based to-be-compared image database. The personal device is coupled to the to-be-compared image providing device and the cloud computing platform and is configured to obtain from the to-be-compared image providing device the to-be-compared hand bone image downloaded by the to-be-compared image providing device and upload this to-be-compared hand bone image to the cloud computing platform. According to the comparison logic, the cloud computing platform receives the to-be-compared hand bone image uploaded by the personal device, compares the to-be-compared hand bone image against the plurality of hand bone images in the bone age model in order to find the hand bone image in the bone age model that is the most similar to the to-be-compared hand bone image, and after finding such a hand bone image, transmits the interpretation data corresponding to that hand bone image to the personal device.

This system allows a physician to use his or her personal device to obtain the reference information required for real-time determination of a consulter's hand bone age so that the hand bone age can be determined accordingly. That is to say, the hospital where the physician works need not be equipped with a costly supercomputer and accurate database, but real-time determination of the hand bone age can be achieved nonetheless.

The present invention also provides a method for determining the hand bone age in real time using a personal device. The method is carried out through the system described above and essentially includes the steps of image preparation, image obtainment, and comparison and interpretation. In the step of image preparation, the to-be-compared image providing device downloads one of the to-be-compared hand bone images in the cloud-based to-be-compared image database. In the step of image obtainment, the personal device obtains from the to-be-compared image providing device the to-be-compared hand bone image downloaded by the to-be-compared image providing device and uploads this to-be-compared hand bone image to the cloud computing platform. In the step of comparison and interpretation, the cloud computing platform executes the comparison logic by comparing the to-be-compared hand bone image uploaded by the personal device against the plurality of hand bone images in the bone age model, with a view to finding the hand bone image in the bone age model that is the most similar to the to-be-compared hand bone image, and by transmitting to the personal device the interpretation data corresponding to the hand bone image found.

The foregoing steps make it possible to determine the hand bone age in real time using a personal device.

BRIEF DESCRIPTION OF THE SEVERAL VIEWS OF THE DRAWINGS

FIG. 3 shows an operation mode of the first preferred embodiment of the invention;

DETAILED DESCRIPTION OF THE INVENTION

Figure 1:
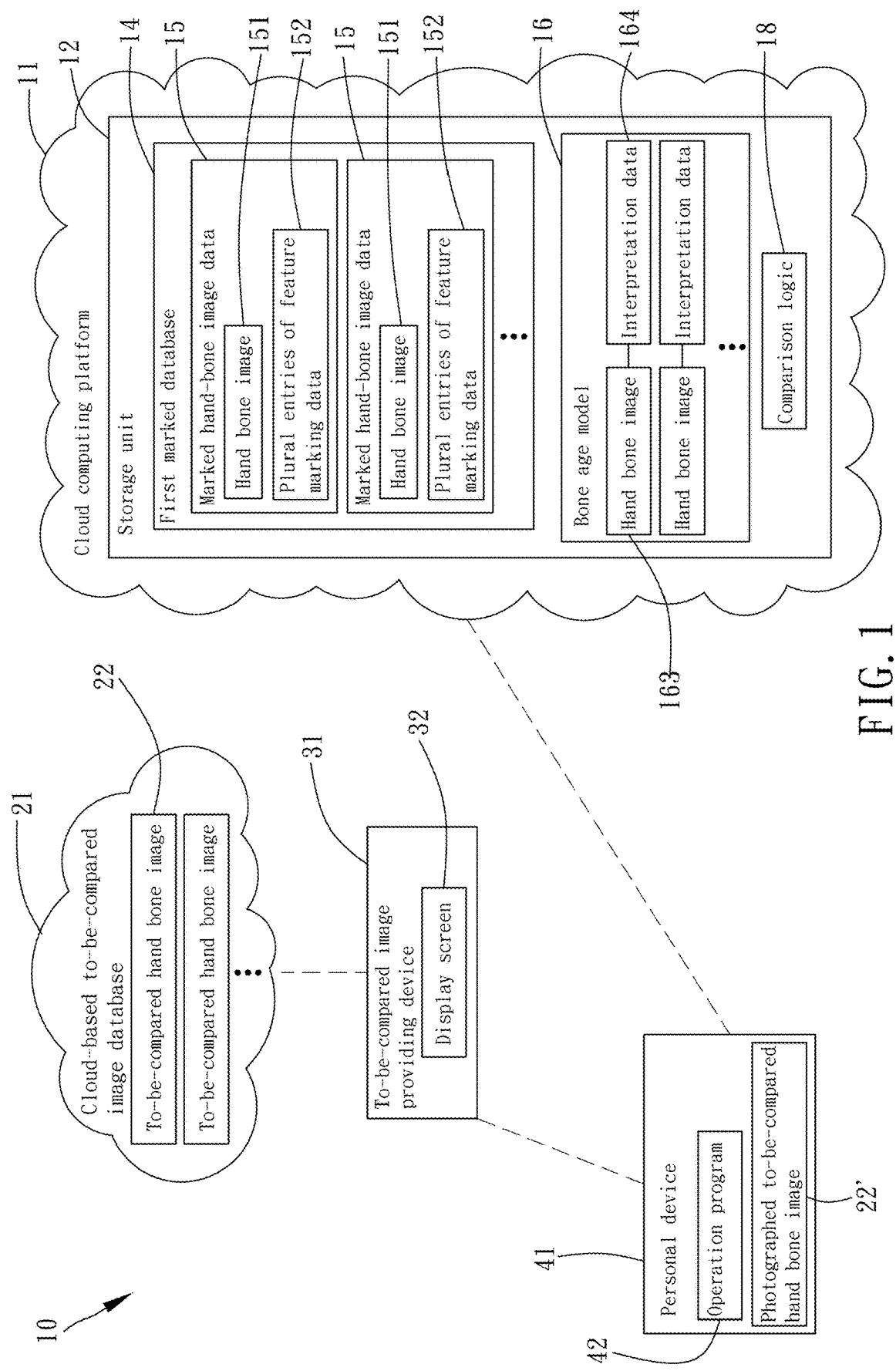
FIG. 1 is a block diagram of the first preferred embodiment of the present invention.

The technical features of the present invention are detailed below with reference to some preferred embodiments and the accompanying drawings.

Referring to FIG. 1 to FIG. 5, the first preferred embodiment of the present invention provides a system 10 for determining the hand bone age in real time using a personal device. The system 10 is composed essentially of a cloud computing platform 11, a cloud-based to-be-compared image database 21, a to-be-compared image providing device 31, and a personal device 41.

Figure 2:
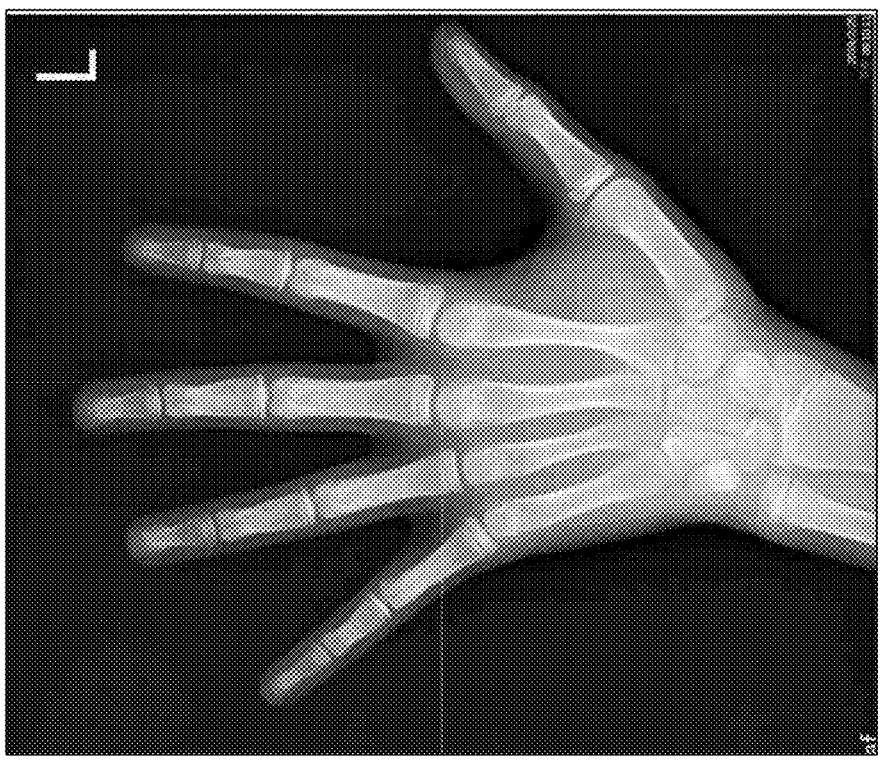
FIG. 2 is an exemplary X-ray hand bone image for use in the first preferred embodiment of the invention.

The cloud computing platform 11 has a storage unit 12. The storage unit 12 stores a first marked database 14, a bone age model 16, and a comparison logic 18 to be executed by the cloud computing platform 11. The first marked database 14 has plural entries of marked hand-bone image data 15. Each entry of marked hand-bone image data 15 has a hand bone image 151 and plural entries of feature marking data 152 corresponding to the hand bone image 151. The plural entries of feature marking data 152 may be the data used by a physician to mark the features of the bones in each hand bone image 151, wherein the features may be, but are not limited to, the proportion, length, size, width, and curvature of each bone and the distances to the adjacent bones. The features may also include the gender and age of the person corresponding to each hand bone image 151. FIG. 2 shows an X-ray hand bone image by way of example. The bone age model 16 is established by training an artificial neural network with the plural entries of marked hand-bone image data 15. The bone age model 16 has a plurality of hand bone images 163 and plural entries of interpretation data 164. The hand bone images 163 correspond to the plural entries of marked hand-bone image data 15 respectively, and the plural entries of interpretation data 164 correspond to the hand bone images 163 respectively. In practice, the cloud computing platform 11 may be a cloud server provided by the establisher of the bone age model 16 or a supercomputer; the present invention has no limitation in this regard, provided that the cloud computing platform 11 offers cloud computing and file/data storage services.

The cloud-based to-be-compared image database 21 stores a plurality of to-be-compared hand bone images 22. In practice, the cloud-based to-be-compared image database 21 may be the cloud database of a hospital, and the to-be-compared hand bone images 22 stored in the cloud-based to-be-compared image database 21 may be the hand bone images generated by the X-ray imaging equipment of the hospital.

The to-be-compared image providing device 31 is coupled to the cloud-based to-be-compared image database 21 and is configured to download one of the to-be-compared hand bone images 22 in the cloud-based to-be-compared image database 21. In practice, the to-be-compared image providing device 31 may be the computer in an examination room of the aforesaid hospital, and once a person (e.g., a patient) whose bone age is to be determined has a hand bone image taken by the X-ray imaging equipment of the hospital, the hand bone image taken is stored in the cloud-based to-be-compared image database 21 as a to-be-compared hand bone image 22 and then downloaded by the computer in the examination room. The to-be-compared image providing device 31 may be provided with a display screen 32 for displaying the to-be-compared hand bone image 22 downloaded by the to-be-compared image providing device 31.

Figure 4:
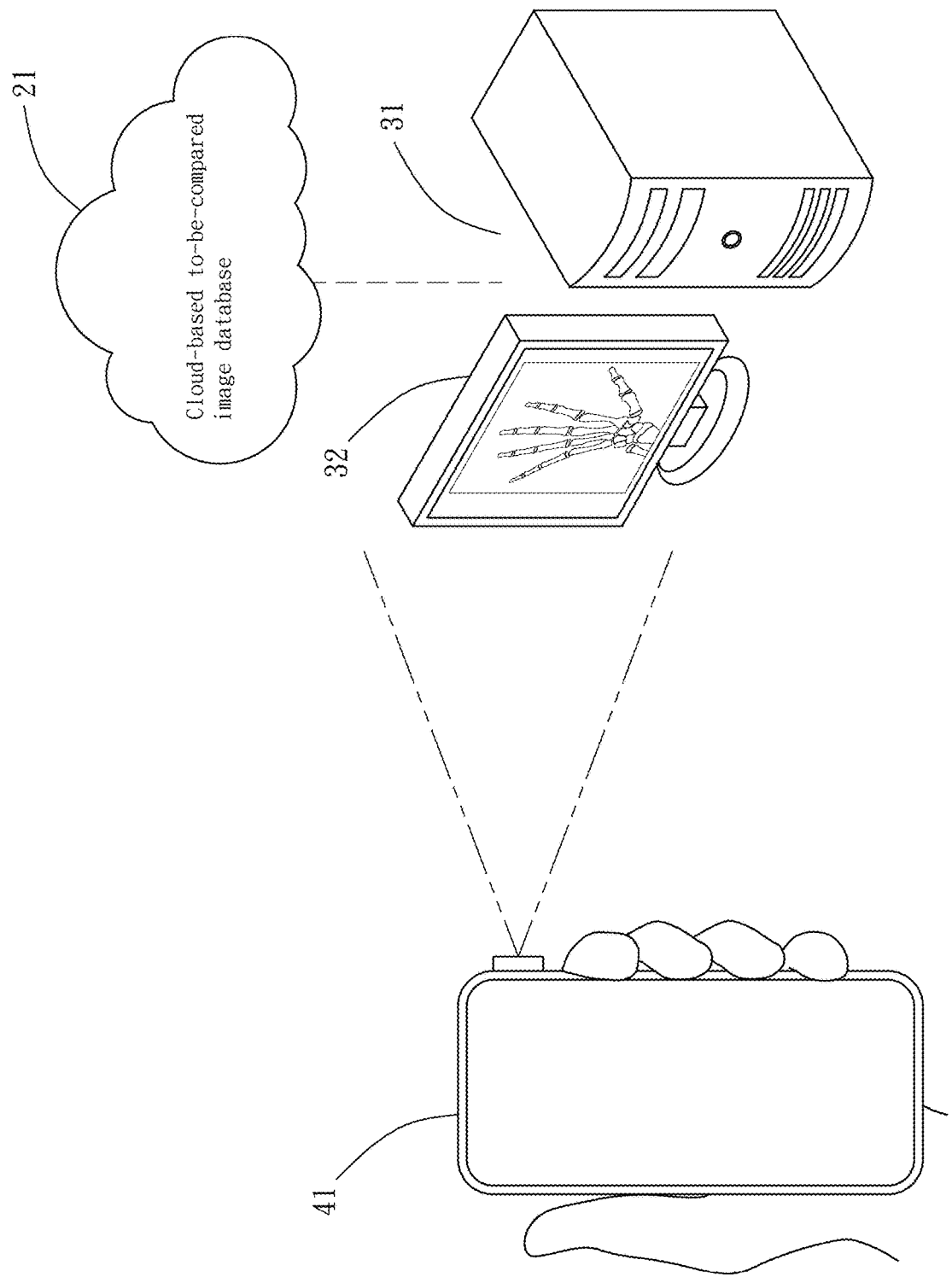
FIG. 4 shows another operation mode of the first preferred embodiment of the invention.

The personal device 41 is coupled to the to-be-compared image providing device 31 and the cloud computing platform 11. The personal device 41 is configured to obtain from the to-be-compared image providing device 31 the to-be-compared hand bone image 22 downloaded by the to-be-compared image providing device 31 and upload this to-be-compared hand bone image 22 to the cloud computing platform 11. In practice, the personal device 41 may be a personal computer or a smartphone, and in a preset scenario, the user of the personal device 41 is generally a person with the qualification of a physician. In FIG. 3, the personal device 41 is implemented as a personal computer and can be connected to the to-be-compared image providing device 31 through a network in order to download from the to-be-compared image providing device 31 the to-be-compared hand bone image 22 downloaded by the to-be-compared image providing device 31 from the cloud-based to-be-compared image database 21. The personal device 41 in FIG. 3 can also be connected to a cloud in order to upload to the cloud computing platform 11 the to-be-compared hand bone image 22 downloaded from the to-be-compared image providing device 31. In FIG. 4, the personal device 41 is implemented as a smartphone instead and can use the camera function of the smartphone to photograph the to-be-compared hand bone image 22 displayed on the display screen 32 of the to-be-compared image providing device 31, thereby obtaining a photographed to-be-compared hand bone image 22', which is then uploaded by the personal device 41 to the cloud computing platform 11 as an alternative for the to-be-compared hand bone image 22 downloaded by the to-be-compared image providing device 31. It is understood that the personal device 41 is generally installed with an operation program 42 to be operated by a user in order for the personal device 41 to obtain from the to-be-compared image providing device 31 the to-be-compared hand bone image 22 downloaded by the to-be-compared image providing device 31 and upload the obtained to-be-compared hand bone image 22 to the cloud computing platform 11.

The comparison logic 18 entails the following operations by the cloud computing platform 11. Upon receiving the to-be-compared hand bone image 22 uploaded by the personal device 41, the cloud computing platform 11 compares this to-be-compared hand bone image 22 against the plurality of hand bone images 163 in the bone age model 16 in order to find the hand bone image 163 that is the most similar to the to-be-compared hand bone image 22. Once that hand bone image 163 is found, the cloud computing platform 11 transmits the interpretation data 164 corresponding to the hand bone image 163 to the personal device 41, in order for the personal device 41 to display the interpretation data 164 using either the display function of the personal device 41 or the corresponding function of the operation program 42. If it is the photographed to-be-compared hand bone image 22' that is uploaded by the personal device 41, the cloud computing platform 11 will compare the photographed to-be-compared hand bone image 22' against the plurality of hand bone images 163 in the bone age model 16.

Figure 5:
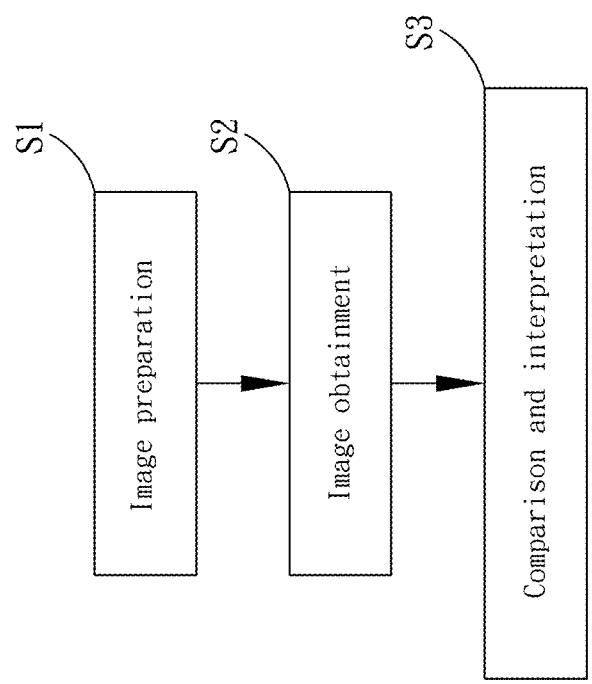
FIG. 5 is a flowchart for the first preferred embodiment of the invention.

Having described the system structure of the first embodiment, the present specification continues to detail the steps of the operation method of the first embodiment with reference to FIG. 5.

Step S1: image preparation. The to-be-compared image providing device 31 downloads one of the to-be-compared hand bone images 22 in the cloud-based to-be-compared image database 21. For example, once a person whose bone age is to be determined has a hand bone image taken by the X-ray imaging equipment of the aforesaid hospital and uploaded to the cloud database of the hospital, the to-be-compared image providing device 31 (e.g., the computer in an examination room of the hospital) downloads the person's to-be-compared hand bone image 22 from the cloud database.

Step S2: image obtainment. The personal device 41 obtains from the to-be-compared image providing device 31 the to-be-compared hand bone image 22 downloaded by the to-be-compared image providing device 31 and uploads the obtained to-be-compared hand bone image 22 to the cloud computing platform 11. More specifically, the personal device 41 obtains the to-be-compared hand bone image 22 downloaded by the to-be-compared image providing device 31 (or the photographed to-be-compared hand bone image 22') by downloading (or photographing) and uploads the to-be-compared hand bone image 22 (or the photographed to-be-compared hand bone image 22') to the cloud computing platform 11.

Step S3: comparison and interpretation. The cloud computing platform 11 executes the comparison logic 18 as follows. The cloud computing platform 11 compares the to-be-compared hand bone image 22 uploaded by the personal device 41 against the plurality of hand bone images 163 in the bone age model 16 in order to find the hand bone image 163 that is the most similar to the to-be-compared hand bone image 22. Once that hand bone image 163 is found, the cloud computing platform 11 transmits the interpretation data 164 corresponding to the hand bone image 163 to the personal device 41. Thus, a physician using the personal device 41 can obtain the interpretation data 164 produced by the cloud computing platform 11 through the aforesaid comparing process and then use the interpretation data 164 as a reference while evaluating the bone age of the person whose bone age is to be determined.

It can be known from the above that, even if a hospital does not have a supercomputer and a dedicated database of accurately marked medical images (e.g., does not have the financial resources to acquire a supercomputer and set up a complete database), the system and method of the first embodiment of the present invention allow a physician working in the hospital to access the cloud computing platform 11 and obtain the reference information required for determining a consulter's bone age. More specifically, the physician can use his or her personal device 41 to obtain in real time the reference information needed to determine the consulter's hand bone age and can therefore produce an accurate determination result rapidly.

Figure 6:
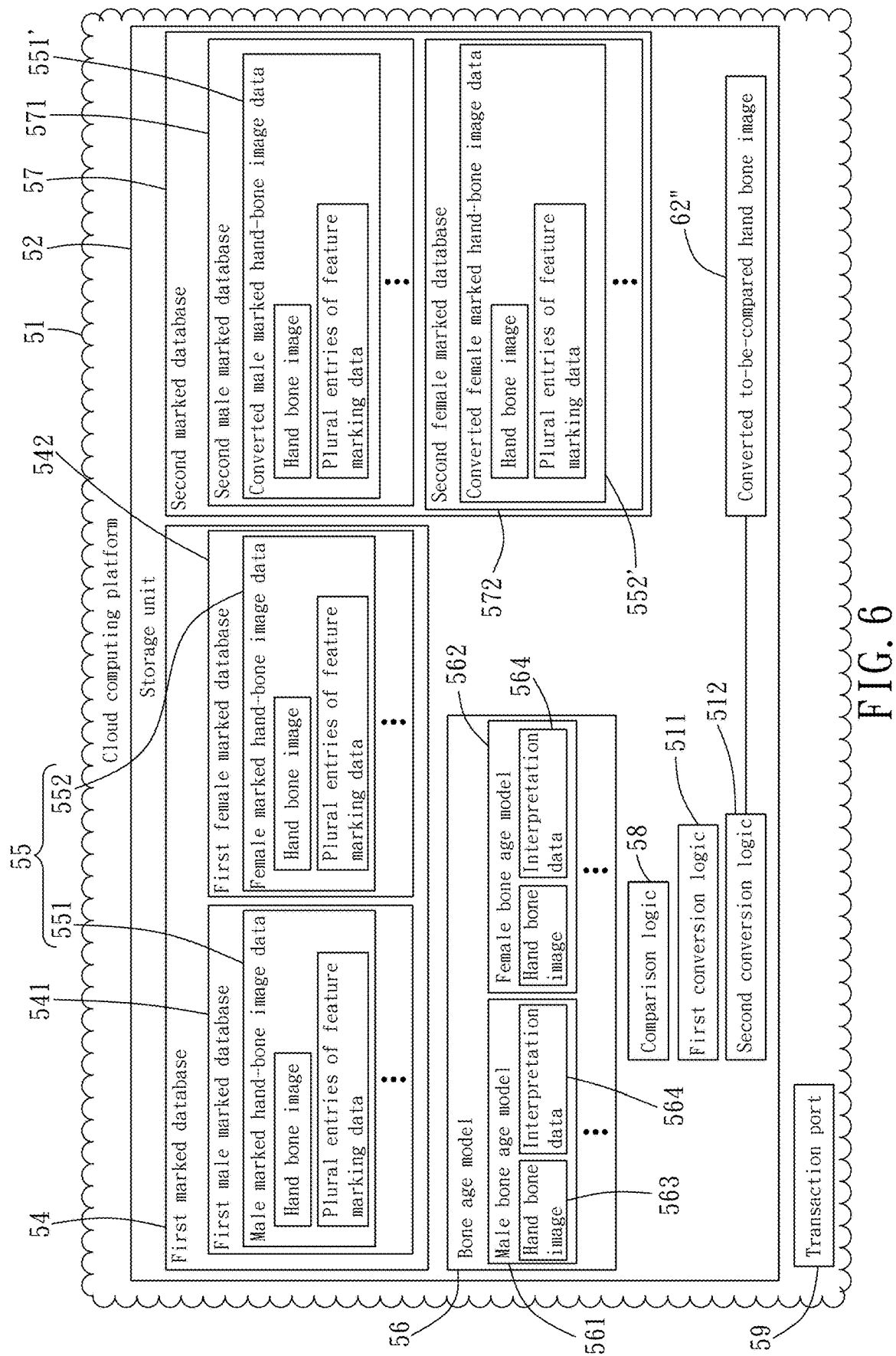
FIG. 6 is a block diagram of the second preferred embodiment of the invention, showing in particular the structure of the cloud computing platform.
Figure 7:
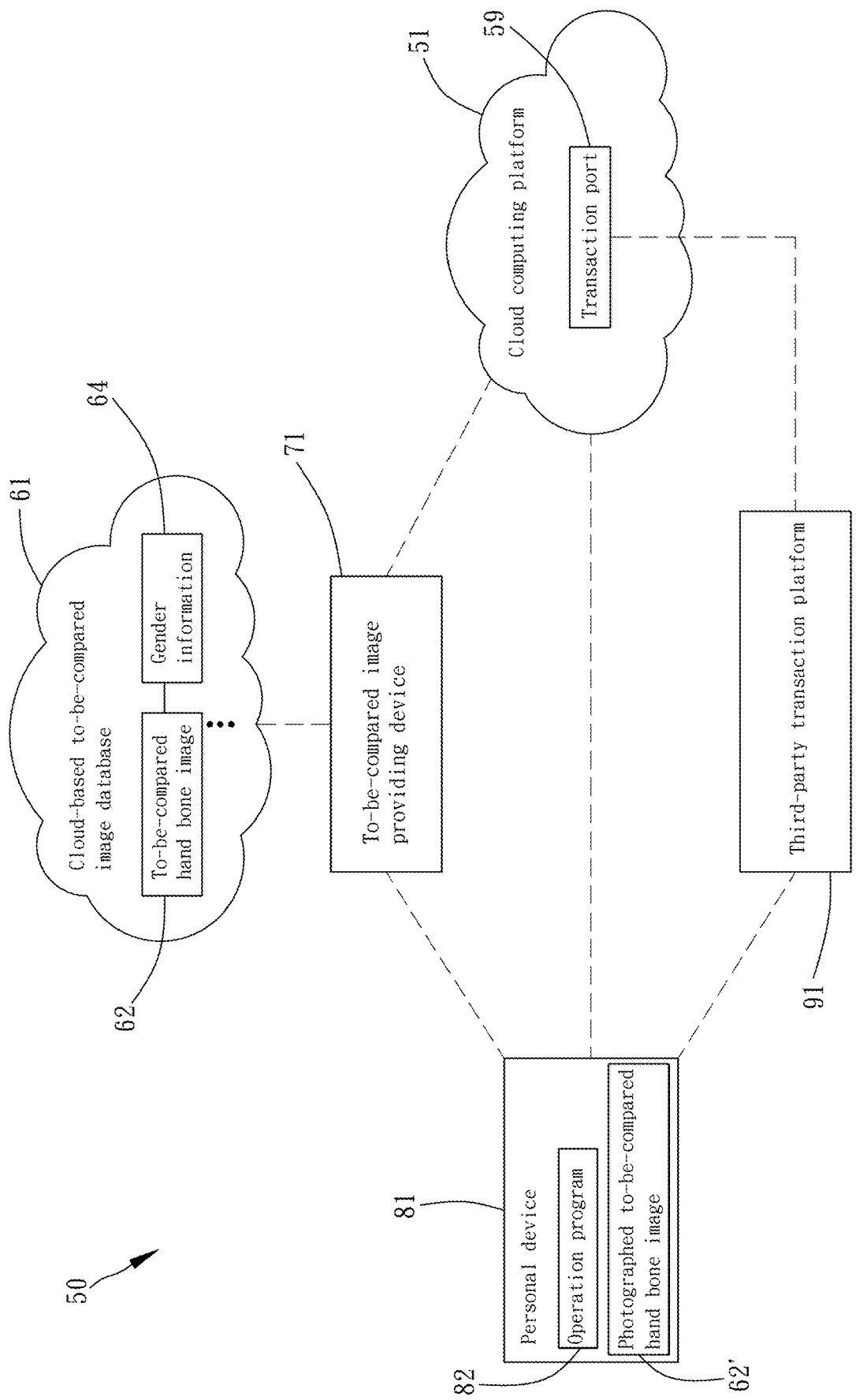
FIG. 7 shows how the second preferred embodiment of the invention operates.
Figure 8:
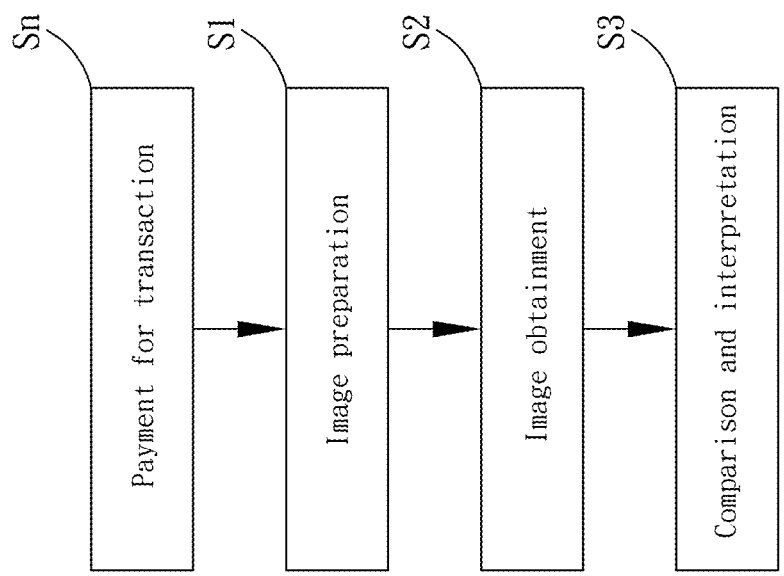
FIG. 8 is a flowchart for the second preferred embodiment of the invention.

FIG. 6 to FIG. 8 show the system 50 for determining the hand bone age in real time using a personal device according to the second preferred embodiment of the present invention. This embodiment is substantially the same as the first embodiment except for the following:

The cloud computing platform 51 further includes a transaction port 59 through which the cloud computing platform 51 can be coupled to a third-party transaction platform 91.

The first marked database 54 is divided into a first male marked database 541 and a first female marked database 542, and the plural entries of marked hand-bone image data 55 are divided into plural entries of male marked hand-bone image data 551 and plural entries of female marked hand-bone image data 552. The plural entries of male marked hand-bone image data 551 are stored in the first male marked database 541 while the plural entries of female marked hand-bone image data 552 are stored in the first female marked database 542.

The bone age model 56 is divided into a male bone age model 561 and a female bone age model 562. The male bone age model 561 is established by training the artificial neural network with the plural entries of male marked hand-bone image data 551, and the female bone age model 562 is established by training the artificial neural network with the plural entries of female marked hand-bone image data 552.

The cloud-based to-be-compared image database 61 stores the gender information 64 corresponding to each to-be-compared hand bone image 62.

The to-be-compared image providing device 71 is configured to download from the cloud-based to-be-compared image database 61 not only one of the to-be-compared hand bone images 62 stored therein, but also the gender information 64 corresponding to that to-be-compared hand bone image 62.

The personal device 81 is configured to obtain from the to-be-compared image providing device 71 both the to-be-compared hand bone image 62 and the gender information 64 downloaded by the to-be-compared image providing device 71, and to upload not only the to-be-compared hand bone image 62 but also the gender information 64 obtained. For example, when implemented as a personal computer, the personal device 81 can simultaneously download through a network the to-be-compared hand bone image 62 and the gender information 64 downloaded by the to-be-compared image providing device 71 and then upload the to-be-compared hand bone image 62 and the gender information 64 at the same time. When implemented as a smartphone, however, the personal device 81 photographs and thereby obtains the photographed to-be-compared hand bone image 62' without downloading the corresponding gender information 64 at the same time. Hence, when the photographed to-be-compared hand bone image 62' is subsequently uploaded, the gender information 64 must be provided manually by the user of the personal device 81, e.g., by inputting the gender information 64 through the operation program 82.

The comparison logic 58 is to compare the to-be-compared hand bone image 62 uploaded by the personal device 81 against the male bone age model 561 or the female bone age model 562, depending on the gender information 64 uploaded by the personal device 81.

In the second embodiment, male and female hand bone images are separated from each other, so the bone age models 561 and 562, the first marked database 54 (or more specifically the first male marked database 541 and the first female marked database 542), and the marked hand-bone image data 551 and 552 are also gender-specific. The distinction between male and female in this embodiment is justified by the typical differences between male hand bone images and female hand bone images and is intended to increase the accuracy of the comparison results.

Furthermore, as X-ray hand bone images are generally high-resolution image files in the DICOM (Digital Imaging and Communications in Medicine) format and therefore have a far larger file size than those taken with a common digital camera, downloading or uploading such an image gives rise to a large amount of network traffic. In light of this, the second embodiment further includes performing data compression and file format conversion on an image file so as to downsize the file and thereby facilitate file transfer, as explained in more detail below.

Given the need for data compression and file format conversion, the cloud computing platform 51 further has, and is configured to execute, a first conversion logic 511 stored in the storage unit 52, wherein the first conversion logic 511 is to subject the plural entries of male marked hand-bone image data 551 and the plural entries of female marked hand-bone image data 552 in the first marked database 54 to a conversion of image file format and to store the plural entries of converted marked hand-bone image data 551' and 552' into a second marked database 57. The conversion of image file format can be carried out by any known data compression and file format conversion techniques, e.g., a technique for converting an image file into the JPEG (Joint Photographic Experts Group) or TIFF (Tagged Image File Format) format. When image files are compressed into the JPEG format, however, the destructive nature of such compression may require that the converted files be restored by a proper restoration method, e.g., by the non-local means algorithm to reduce image noise.

The second marked database 57 is stored in the storage unit 52 and is divided into a second male marked database 571 and a second female marked database 572 for storing the plural entries of converted (i.e., image file format-converted) male marked hand-bone image data 551' and the plural entries of converted (i.e., image file format-converted) female marked hand-bone image data 552' respectively. The male bone age model 561 is established by training the artificial neural network with the plural entries of converted male marked hand-bone image data 551' in the second marked database 57, and the female bone age model 562 is established by training the artificial neural network with the plural entries of converted female marked hand-bone image data 552' in the second marked database 57.

The cloud computing platform 51 further has, and is configured to execute, a second conversion logic 512 stored in the storage unit 52, wherein the second conversion logic 512 is to subject the to-be-compared hand bone image 62 uploaded by the personal device 81 to a conversion of image file format and thereby produce a converted to-be-compared hand bone image 62". Accordingly, the comparison logic 58 is to compare the converted to-be-compared hand bone image 62" against the plurality of hand bone images 563 in the male bone age model 561 or in the female bone age model 562, depending on the gender information 64 (i.e., male or female) uploaded by the personal device 81.

Having stated the structural differences between the first embodiment and the second embodiment, the present specification continues to detail the operation method of the second embodiment. The operation method of the second embodiment is substantially the same as that of the first embodiment except for the following:

Referring to FIG. 8, the additional step Sn of payment for transaction is performed prior to step S2 of image obtainment. In step Sn, the personal device 81 is coupled to the third-party transaction platform 91 and pays a fee, and the cloud computing platform 51 is coupled to the third-party transaction platform 91 through the transaction port 59 and checks with the third-party transaction platform 91 whether the personal device 81 has paid the fee or not. In step S2 of image obtainment, therefore, the cloud computing platform 51 may receive, or refuse to receive, the to-be-compared hand bone image 62 uploaded by the personal device 81, depending on whether the personal device 81 has paid the fee or not, and in step S3 of comparison and interpretation, the cloud computing platform 51 may transmit, or refuse to transmit, the interpretation data 564 to the personal device 81, depending also on whether the personal device 81 has paid the fee or not.

Step Sn of payment for transaction must precede step S2 of image obtainment but may precede or follow step S1 of image preparation. In the second embodiment, step Sn is performed prior to step S1 by way of example. Step Sn of payment for transaction is intended mainly to furnish a payment mechanism for the real-time bone age determination service provided by the system of the present invention, the objective being to provide the real-time determination service only to those who have paid the required fee.

It can be known from the above that the second embodiment divides hand bone images by gender to increase the accuracy of hand bone age determination, that the additional data compression/restoration function helps reduce network traffic, and that the transaction fee payment mechanism embodies the "user pays" principle and thereby provides a win-win situation for the system provider and system users.

The remaining technical features and effects of the second embodiment can be known from the foregoing description of the first embodiment and hence will not be stated repeatedly.

What is claimed is:

1. A system for real-time determination of a hand bone age using a personal device, comprising:
    a cloud computing platform having a storage unit, wherein the storage unit stores a first marked database, a bone age model, and a comparison logic, the cloud computing platform is configured to execute the comparison logic, the first marked database has plural entries of marked hand-bone image data, each said entry of marked hand-bone image data at least has a hand bone image and plural entries of feature marking data corresponding to the hand bone image, the bone age model is established by training an artificial neural network with the plural entries of marked hand-bone image data, and the bone age model has a plurality of hand bone images corresponding respectively to the plural entries of marked hand-bone image data and has interpretation data corresponding to each said hand bone image in the bone age model;
    a cloud-based to-be-compared image database storing a plurality of to-be-compared hand bone images;

a to-be-compared image providing device coupled to the cloud-based to-be-compared image database and configured to download a said to-be-compared hand bone image in the cloud-based to-be-compared image database; and the personal device, which is coupled to the to-be-compared image providing device and the cloud computing device and is configured to obtain from the to-be-compared image providing device the to-be-compared hand bone image downloaded by the to-be-compared image providing device and upload this to-be-compared hand bone image to the cloud computing platform;

wherein the comparison logic is for the cloud computing platform to, upon receiving the to-be-compared hand bone image uploaded by the personal device, compare this to-be-compared hand bone image against the plurality of hand bone images in the bone age model in order to find a said hand bone image in the bone age model that is the most similar to the to-be-compared hand bone image, and for the cloud computing platform to transmit to the personal device the interpretation data corresponding to the hand bone image found.

2. The system for real-time determination of the hand bone age using the personal device as claimed in claim 1, wherein the first marked database is divided into a first male marked database and a first female marked database, the plural entries of marked hand-bone image data are divided into plural entries of male marked hand-bone image data and plural entries of female marked hand-bone image data, the plural entries of male marked hand-bone image data are stored in the first male marked database, the plural entries of female marked hand-bone image data are stored in the first female marked database, the bone age model is divided into a male bone age model and a female bone age model, the male bone age model is established by training the artificial neural network with the plural entries of male marked hand-bone image data, the female bone age model is established by training the artificial neural network with the plural entries of female marked hand-bone image data, the cloud-based to-be-compared image database stores gender information corresponding to each said to-be-compared hand bone image, the to-be-compared image providing device is configured to download from the cloud-based to-be-compared image database a said to-be-compared hand bone image and the corresponding gender information, the personal device is configured to obtain from the to-be-compared image providing device the to-be-compared hand bone image and the corresponding gender information downloaded by the to-be-compared image providing device and upload this to-be-compared hand bone image and the corresponding gender information to the cloud computing platform, and the comparison logic is to compare the to-be-compared hand bone image uploaded by the personal device against the male bone age model or the female bone age model, depending on the corresponding gender information uploaded by the personal device.

3. The system for real-time determination of the hand bone age using the personal device as claimed in claim 2, wherein the cloud computing platform further has, and is configured to execute, a first conversion logic stored in the storage unit, the first conversion logic is to perform image file format conversion on the plural entries male marked hand-bone image data and the plural entries of female marked hand-bone image data in the first marked database and store plural entries of converted male marked hand-bone image data and plural entries of converted female marked hand-bone image data in a second marked database, the second marked database is stored in the storage unit and is divided into a second male marked database for storing the plural entries of converted male marked hand-bone image data and a second female marked database for storing the plural entries of converted female marked hand-bone image data, the male bone age model is established by training the artificial neural network with the plural entries of converted male marked hand-bone image data in the second marked database, and the female bone age model is established by training the artificial neural network with the plural entries of converted female marked hand-bone image data in the second marked database.

4. The system for real-time determination of the hand bone age using the personal device as claimed in claim 3, wherein the cloud computing platform further has, and is configured to execute, a second conversion logic stored in the storage unit, the second conversion logic is to perform image file format conversion on the to-be-compared hand bone image uploaded by the personal device and thereby produce a converted to-be-compared hand bone image, and the comparison logic is to compare the converted to-be-compared hand bone image against the plurality of hand bone images in the bone age model.

5. The system for real-time determination of the hand bone age using the personal device as claimed in claim 1, wherein the to-be-compared image providing device has a display screen and displays thereon the to-be-compared hand bone image downloaded by the to-be-compared image providing device, the personal device is a smartphone with a camera function, the personal device obtains a photographed to-be-compared hand bone image by photographing the to-be-compared hand bone image displayed on the display screen and uploads the photographed to-be-compared hand bone image to the cloud computing platform in place of the to-be-compared hand bone image downloaded by the to-be-compared image providing device, and the comparison logic is for the cloud computing platform to, upon receiving the photographed to-be-compared hand bone image uploaded by the personal device, compare the photographed to-be-compared hand bone image against the plurality of hand bone images in the bone age model.

6. The system for real-time determination of the hand bone age using the personal device as claimed in claim 1, wherein the personal device is installed with an operation program to be operated by a user, and the personal device executes the operation program to obtain from the to-be-compared image providing device the to-be-compared hand bone image downloaded by the to-be-compared image providing device, to uploaded this to-be-compared hand bone image to the cloud computing platform, and to display the interpretation data transmitted by the cloud computing platform upon receiving the interpretation data.

7. The system for real-time determination of the hand bone age using the personal device as claimed in claim 1, wherein the cloud computing platform further comprises a transaction port in order to be coupled to a third-party transaction platform through the transaction port.

8. A method for real-time determination of a hand bone age using a personal device, wherein the method is performed through the system claimed in claim 1 and comprises the steps of:
   image preparation, in which step the to-be-compared image providing device downloads a said to-be-compared hand bone image from the cloud-based to-be-compared image database;

image obtainment, in which step the personal device obtains from the to-be-compared image providing device the to-be-compared hand bone image downloaded by the to-be-compared image providing device and uploads this to-be-compared hand bone image to the cloud computing platform; and comparison and interpretation, in which step the cloud computing platform executes the comparison logic by comparing the to-be-compared hand bone image uploaded by the personal device against the plurality of hand bone images in the bone age model in order to find a said hand bone image in the bone age model that is the most similar to the to-be-compared hand bone image, and by transmitting to the personal device the interpretation data corresponding to the hand bone image found.

9. The method for real-time determination of the hand bone age using the personal device as claimed in claim 8, wherein in the step of image preparation, the to-be-compared image providing device displays the to-be-compared hand bone image downloaded by the to-be-compared image providing device on a display screen of the to-be-compared image providing device; in the step of image obtainment, the personal device, implemented as a smartphone with a camera function, obtains a photographed to-be-compared hand bone image by photographing the to-be-compared hand bone image displayed on the display screen and uploads the photographed to-be-compared hand bone image to the cloud computing platform in place of the to-be-compared hand bone image downloaded by the to-be-compared image providing device; and in the step of comparison and interpretation, the cloud computing platform compares the photographed to-be-compared hand bone image uploaded by the personal device against the plurality of hand bone images in the bone age model upon receiving the photographed to-be-compared hand bone image.

10. The method for real-time determination of the hand bone age using the personal device as claimed in claim 8, further comprising the step, to be performed prior to the step of image obtainment, of payment for transaction, in which step the personal device is coupled to a third-party transaction platform and pays a fee and the cloud computing platform is coupled to the third-party transaction platform through a transaction port of the cloud computing platform and checks with the third-party transaction platform whether the personal device has paid the fee or not, wherein in the step of image obtainment, the cloud computing platform determines whether to receive the to-be-compared hand bone image uploaded by the personal device or not based on whether the personal device has paid the fee or not; and in the step of comparison and interpretation, the cloud computing platform determines whether to transmit the interpretation data to the personal device or not based on whether the personal device has paid the fee or not.

* * * * *